(12) United States Patent
Wong et al.

(10) Patent No.: US 10,123,843 B2
(45) Date of Patent: Nov. 13, 2018

(54) INPUT DEVICE FOR CONTROLLING A CATHETER

(71) Applicant: Auris Health, Inc., Redwood City, CA (US)

(72) Inventors: Serena Wong, Menlo Park, CA (US); Richard Henderson, Fremont, CA (US); June Park, San Jose, CA (US); Sean Walker, Fremont, CA (US); Jason Hsu, Mountain View, CA (US); Kamini Balaji, Sunnyvale, CA (US); Leena Kadakia, Foster City, CA (US); Kiran Murthy, Sunnyvale, CA (US)

(73) Assignee: AURIS HEALTH, INC., Redwood City, CA (US)

( * ) Notice: Subject to any disclaimer, the term of this patent is extended or adjusted under 35 U.S.C. 154(b) by 64 days.

(21) Appl. No.: 15/393,898

(22) Filed: Dec. 29, 2016

(65) Prior Publication Data
US 2017/0105803 A1 Apr. 20, 2017

Related U.S. Application Data

(63) Continuation of application No. 13/832,866, filed on Mar. 15, 2013.

(51) Int. Cl.
*A61B 34/00* (2016.01)
*A61M 25/01* (2006.01)
*A61M 25/09* (2006.01)
*A61B 34/30* (2016.01)
*A61B 34/10* (2016.01)

(52) U.S. Cl.
CPC .............. *A61B 34/25* (2016.02); *A61B 34/10* (2016.02); *A61B 34/30* (2016.02); *A61B 34/71* (2016.02); *A61M 25/0147* (2013.01); *A61M 25/09* (2013.01); *A61B 2034/102* (2016.02); *A61B 2034/301* (2016.02); *A61M 2205/505* (2013.01)

(58) Field of Classification Search
CPC ......... A61B 34/25; A61B 34/10; A61B 34/30; A61B 2034/102; A61M 25/09; A61M 25/0147; A61M 2205/505
See application file for complete search history.

(56) References Cited

U.S. PATENT DOCUMENTS

| 4,700,693 A | 10/1987 | Lia et al. |
| 5,398,691 A | 3/1995 | Martin et al. |
| 5,408,409 A | 4/1995 | Glassman et al. |

(Continued)

FOREIGN PATENT DOCUMENTS

WO WO 03086190 A1 10/2003

*Primary Examiner* — Bradley J Osinski
(74) *Attorney, Agent, or Firm* — Knobbe Martens Olson & Bear LLP (57) ABSTRACT

An input device includes a plurality of orientation blocks each representing a portion of a catheter assembly and a controller configured to determine an orientation of the plurality of orientation blocks relative to one another. The controller is further configured to output a control signal that causes a tip of a catheter assembly to adopt the orientation determined by the controller. A system includes an actuator configured to manipulate a position and orientation of the catheter assembly. The controller of the input device is configured to output a control signal to the actuator to make a tip of a catheter assembly adopt the orientation determined by the controller. The input device can be virtually represented on a computing device.

20 Claims, 8 Drawing Sheets

(56) References Cited

U.S. PATENT DOCUMENTS

| | | |
|---|---|---|
| 5,524,180 A | 6/1996 | Wang |
| 5,631,973 A | 5/1997 | Green |
| 5,666,503 A | 9/1997 | Campanelli et al. |
| 5,713,946 A | 2/1998 | Ben-Haim |
| 5,749,362 A | 5/1998 | Funda et al. |
| 5,859,934 A | 1/1999 | Green |
| 5,876,325 A | 3/1999 | Mizuno et al. |
| 5,951,475 A | 9/1999 | Gueziec et al. |
| 6,226,543 B1 | 5/2001 | Gilboa et al. |
| 6,259,806 B1 | 7/2001 | Green |
| 6,272,371 B1 | 8/2001 | Shlomo |
| 6,424,885 B1 | 7/2002 | Niemeyer et al. |
| 6,726,675 B1 | 4/2004 | Beyar |
| 7,155,315 B2 | 12/2006 | Niemeyer et al. |
| 7,594,925 B2 | 9/2009 | Danek |
| 8,343,171 B2 | 1/2013 | Farritor et al. |
| 2006/0025676 A1 | 2/2006 | Viswanathan et al. |
| 2006/0156851 A1 | 7/2006 | Jacobsen et al. |
| 2009/0137952 A1 | 5/2009 | Ramamurthy |
| 2010/0121269 A1 | 5/2010 | Goldenberg |
| 2012/0172666 A1 | 7/2012 | Lawrence et al. |
| 2012/0283819 A1 | 11/2012 | Taylor et al. |

INPUT DEVICE FOR CONTROLLING A CATHETER

CROSS-REFERENCE TO RELATED APPLICATION

This application is a continuation of U.S. patent application Ser. No. 13/832,866, filed Mar. 15, 2013 and entitled "INPUT DEVICE FOR CONTROLLING A CATHETER." The entirety of which is hereby incorporated by reference for all purposes.

BACKGROUND

Robotically controlled catheter systems allow clinicians to direct catheters to various locations within a patient's body. Once in place, the catheter can be manipulated to treat various diseases or help a clinician perform various surgical procedures. For instance, balloon catheters may be used during an angioplasty procedure to widen or clear obstructed arteries. Other types of catheters may be used to administer drugs to a patient or to facilitate the draining of bodily fluids (e.g., a Foley catheter).

SUMMARY

An exemplary input device includes a plurality of orientation blocks that each represent a portion of a catheter assembly and a controller that determines an orientation of the plurality of orientation blocks relative to one another and outputs a control signal that causes a tip of a catheter assembly to adopt the orientation determined by the controller.

An exemplary system includes the input device and an actuator that can manipulate a position and orientation of the catheter assembly. The controller of the input device outputs a control signal to the actuator. The control signal causes a tip of a catheter assembly to adopt the orientation determined by the controller.

Another exemplary system includes a user interface device that presents a representation of a virtual catheter tip and receives a user input associated with manipulating a shape of the virtual catheter tip. A controller is configured to determine a desired shape of the tip of a physical catheter based on the user input and output a control signal that causes a tip of the physical catheter to adopt the shape of the virtual catheter tip.

DETAILED DESCRIPTION

An exemplary input device for a robotically controlled catheter system includes a plurality of orientation blocks that each represent a portion of a catheter assembly and a controller that determines an orientation of the plurality of orientation blocks relative to one another and outputs a control signal that causes a tip of a catheter assembly to adopt the orientation determined by the controller. An exemplary system includes the input device and an actuator that can manipulate a position and orientation of the catheter assembly. The controller of the input device outputs a control signal to the actuator. The control signal causes a tip of a catheter assembly to adopt the orientation determined by the controller. Another exemplary system includes a user interface device that presents a representation of a virtual catheter tip and receives a user input associated with manipulating a shape of the virtual catheter tip. A controller is configured to determine a desired shape of the tip of a physical catheter based on the user input and output a control signal that causes a tip of the physical catheter to adopt the shape of the virtual catheter tip. The input devices described herein, whether physical or virtual, provide a clinician with options for manipulating a position, orientation, or both, of a catheter assembly.

The Figures illustrate exemplary components of a system for manipulating the position and orientation of a catheter assembly. The system may take many different forms and include multiple and/or alternate components and facilities. While an exemplary system is shown, the exemplary components illustrated are not intended to be limiting. Indeed, additional or alternative components and/or implementations may be used. Moreover, some components illustrated in the Figures have been simplified for purposes of clarity. Therefore, the components are not necessarily drawn to scale and certain aspects of some component may be omitted.

Figure 1:
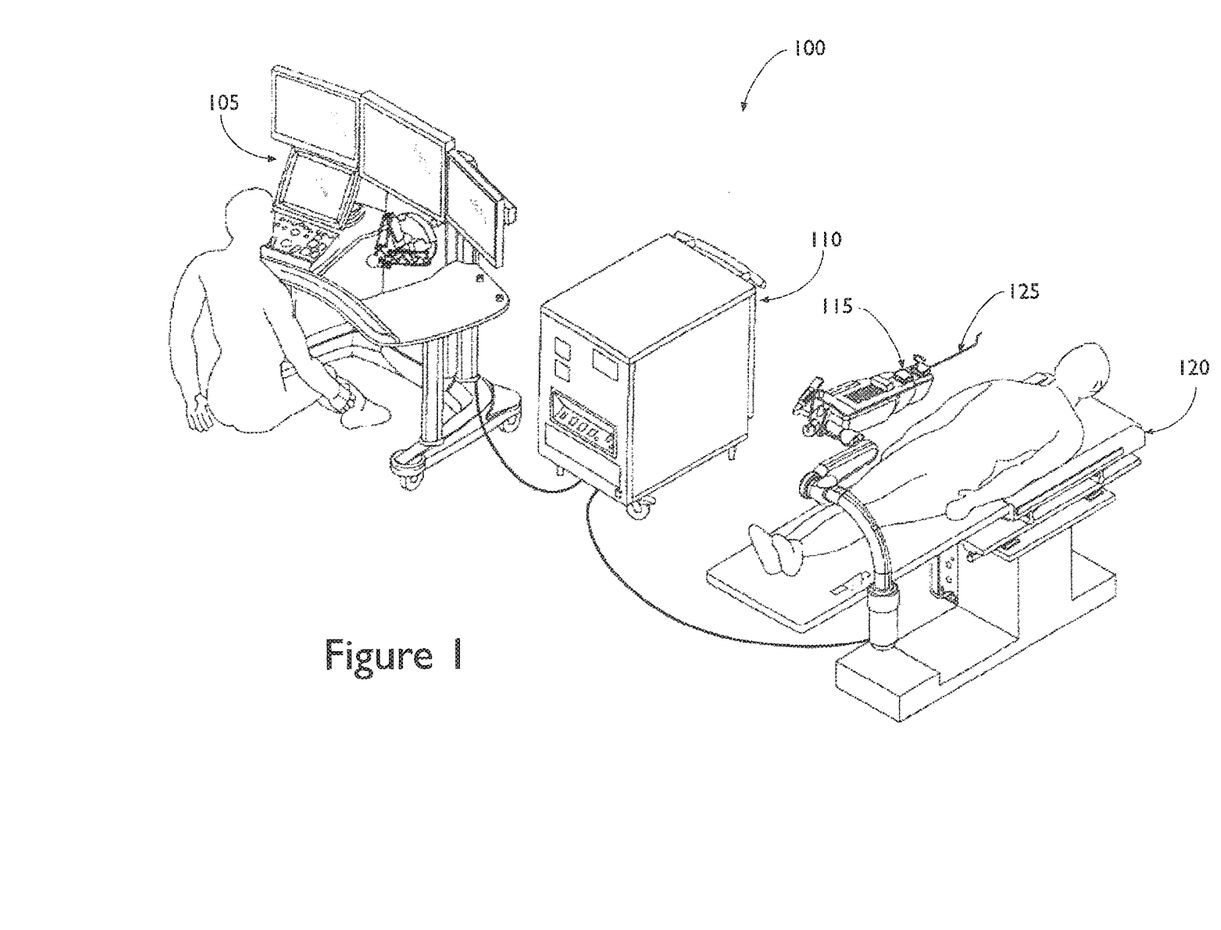
FIG. 1 illustrates an exemplary robotically controlled catheter system.

As illustrated in FIG. 1, the system 100 includes an operator workstation 105, an electronics rack 110, and an instrument driver 115. During use, a patient may be positioned on an operating table 120 or in a surgical bed to which the instrument driver 115 may be coupled or mounted. A clinician may be seated at the operator workstation 105 and can monitor the surgical procedure, patient vitals, and control one or more catheter assemblies. The instrument driver 115 may move the catheter assembly 125 in accordance with the clinician's inputs to the operator workstation 105. Components of the system 100 may communicate with one another through a wired network, a wireless network, or a combination of wired and wireless networks. Communication between some components may be implemented over a packet-switched network such as the Internet.

Figure 2:
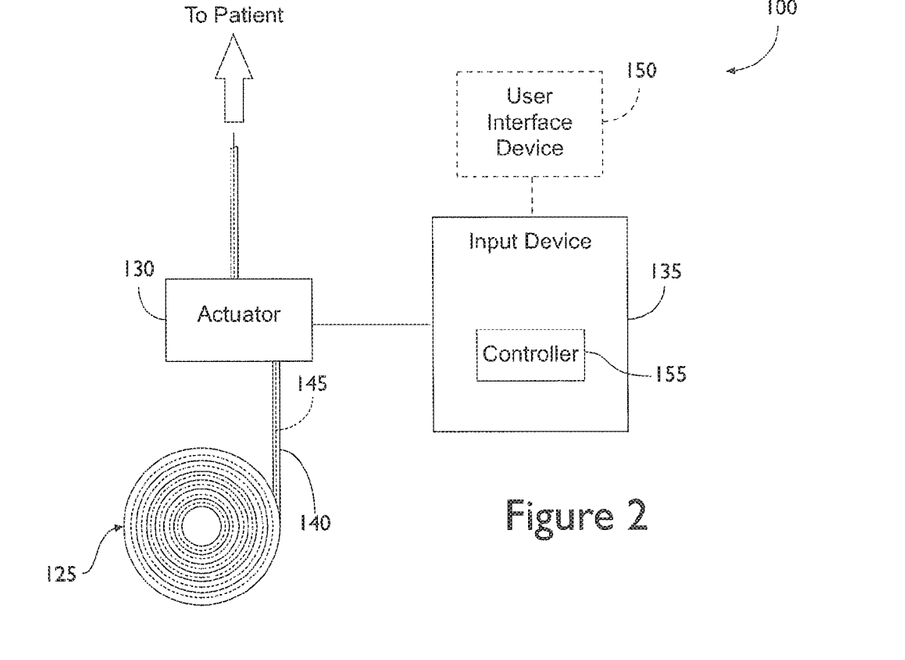
FIG. 2 is a block diagram of exemplary components of the robotically controlled catheter system of claim 1.

Referring now to FIG. 2, the system 100 includes a catheter assembly 125, an actuator 130, and an input device 135.

The catheter assembly 125 may include a catheter 140 and a guide wire 145. The catheter 140 may include a generally hollow tube having sufficient flexibility to travel through a patient's body during, e.g., surgical procedures or other medical treatments. Different types of catheters 140 may be configured to travel through different parts of the patient's body. For instance, a catheter 140 for performing angioplasty procedures may have a different size and flexibility than a catheter 140 used to administer drugs or drain bodily fluids. The catheter 140 may also carry any number of medical instruments (not shown) such as a balloon, stent, or physiological sensors.

The guide wire 145 may be disposed within the catheter 140 and configured to facilitate movement of the catheter 140 through the patient's body. The catheter 140 and guide wire 145 may move through the patient together or the catheter 140 and guide wire 145 may move independently of one another. For instance, the catheter 140 and guide wire 145 may be inserted together into the patient's body until the catheter assembly 125 reaches a surgical site. Once positioned, the guide wire 145 may be removed and the catheter 140 may remain to deploy any medical instruments carried by the catheter 140.

The components of the catheter assembly 125 may be manipulated as the catheter assembly 125 moves throughout the patient's body. As used in the following discussion, the term "advance" may refer to pushing the catheter assembly 125, which may cause any part of the catheter assembly 125 to move further into a patient's body, and the term "retract" may refer to pulling the catheter assembly 125, which may cause any part of the catheter assembly 125 to be removed from the patient's body. Portions of the catheter assembly 125 may be configured to bend relative to other portions. For instance, the tip of the catheter 140, guide wire 145, or both, may be configured to bend relative to the body of the catheter 140, guide wire 145, or both. The catheter assembly 125 may be further configured to rotate, as discussed below.

The actuator 130 may include any device configured to facilitate the movement of the catheter assembly 125 through the patient's body. In one possible implementation, the actuator 130 may be part of the instrument driver 115 shown in FIG. 1. The actuator 130 may be configured cause the catheter assembly 125 to advance or retract relative to the patient's body. Moreover, the actuator 130 may cause the catheter assembly 125 to rotate or for portions of the catheter assembly 125 to bend relative to other portions. The actuator 130 may include any number of components configured to manipulate the position and orientation of the components of the catheter assembly 125. In one possible implementation, the actuator 130 may be configured to receive control signals from, e.g., the input device 135, and manipulate the position and orientation of the components of the catheter assembly 125 accordingly. For instance, the actuator 130 may be configured to receive an advance signal and push the catheter 140, the guide wire 145, or both, further into the patient's body in accordance with the advance signal. The actuator 130 may be configured to receive a retract signal and pull at least part of the catheter 140, the guide wire 145, or both, from the patient's body in accordance with the retract signal. The actuator 130 may be configured to receive a rotate signal and rotate the catheter 140, the guide wire 145, or both, in accordance with the rotate signal. The actuator 130 may include any number of components (not shown) to push, pull, and rotate the components of the catheter assembly 125. For instance, one or more motors (not shown) may be configured to feed (i.e., push) the catheter assembly 125 and the same or different motors may be configured to pull the catheter assembly 125 from the patient. Moreover, the actuator 130 may include wires (not shown) connected to various portions of the catheter assembly 125 that when pulled, cause portions of the catheter assembly 125 to bend in various directions. The actuator 130 may include motors that wind the wires to change the distance between the between the motor and the portion of the catheter assembly 125 to which of the wire is connected. Separate motors may control each wire, thus allowing the actuator 130 to manipulate different parts of the catheter assembly 125 differently.

The input device 135 may be configured to allow a clinician or other medical personnel to control the position and orientation of the catheter assembly 125 within the patient. The input device 135 may be located at the operator workstation 105 and may be configured to receive an input from the clinician based on the way the clinician physically manipulates the shape of the input device 135, position of components of the input device 135, or through a user interface device 150. The user interface device 150 may include, e.g., a touchscreen display configured to present a graphical user interface to the clinician as well as receive user inputs. Example interfaces that may be presented by the user interface are discussed below with respect to FIGS. 7-11. The user interface device 150 may be incorporated into the input device 135 or may be a separate component at the operator workstation 105 shown in FIG. 1. The input device 135 provides the clinician with multiple degrees of freedom, each associated with a different movement of the catheter assembly 125, so that the clinician can control the catheter assembly 125 as if the clinician were manipulating the position and orientation of the catheter assembly 125 directly.

The input device 135 may include a controller 155 configured to interpret the input from the clinician and generate and output corresponding signals to the actuator 130. The controller 155 may be configured to generate an advance signal when the clinician indicates a desire to push the catheter assembly 125 into the patient's body. The controller 155 may be further configured to generate a retract signal when the clinician indicates a desire to pull at least a portion of the catheter assembly 125 from the patient's body. Moreover, the controller 155 may be configured to generate a rotate signal when the clinician indicates a desire to rotate the catheter assembly 125. As discussed above, the clinician's desire for controlling the catheter assembly 125 may be expressed through the input device 135. The controller 155 may interpret these movements based on the outputs of various sensors of the input device 135. FIGS. 3-11 illustrate exemplary components of the input device 135 that the controller 155 may use to determine the clinician's desired manipulation of the catheter assembly 125. The exemplary input devices 135 shown in FIGS. 3-11 are configured to control the position and orientation of the catheter 140, the guide wire 145, or both.

Figures 3, 4, 5:
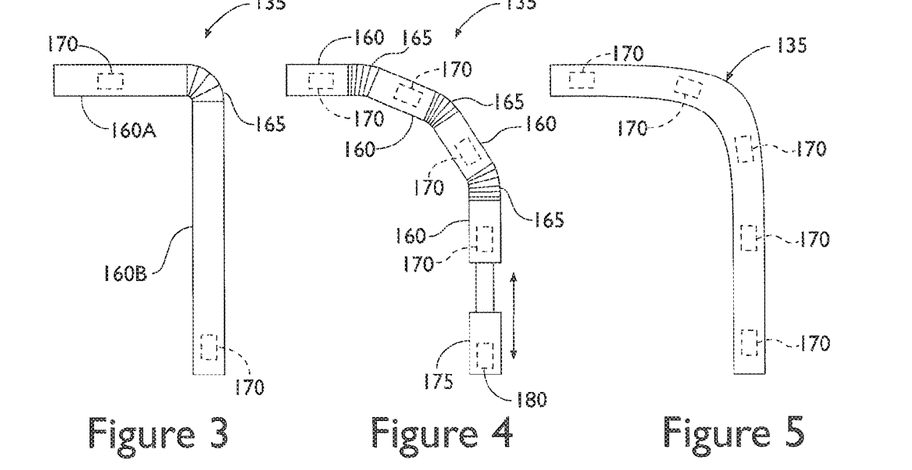
FIG. 3 illustrates an exemplary input device that may be used with the robotically controlled catheter system of FIG. 1.
FIG. 4 illustrates another exemplary input device.
FIG. 5 illustrates yet another exemplary input device.

FIGS. 3-5 illustrate exemplary input devices 135. Referring to FIG. 3, the input device 135 includes two orientation blocks 160 connected by a joint 165. The joint 165 may be formed from a flexible material and configured to permit articulation of one orientation block 160 relative to another orientation block 160. Each orientation block 160 may represent at least a portion of a catheter assembly 125, such as a tip of the catheter assembly 125. A first orientation block 160A may represent one end of the tip and a second orientation block 160B may represent another end of the tip. The first orientation block 160A may represent the end of the tip that travels the furthest inside the patient during a surgical procedure.

Each orientation block 160 may include an orientation sensor 170 configured to output an orientation signal representing an orientation. The orientation sensor 170 may include, e.g., a gyroscope, accelerometer, encoder, or potentiometer. The signal output by the orientation sensor 170 may define an orientation relative to a reference point. The orientation signal, therefore, may indicate whether the orientation block 160 has been turned, rotated, moved, or otherwise manipulated. The orientation sensor 170 may output the orientation signal to the controller 155, which may be configured to determine the orientation of each block.

In one possible approach, the joint 165 may include the orientation sensor 170. For instance, the joint 165 may incorporate a potentiometer or a transducer configured to detect the change in orientation of two orientation blocks 160 relative to one another when the potentiometer or transducer is placed between the two orientation blocks 160. In general, the potentiometer or transducer may be configured to detect movement in a particular direction based on angle measurements relative to a plane measured.

The controller 155 may be configured to associate each orientation block 160 with a part of the tip of the catheter 140 by, e.g., determining a position of each orientation block 160 in the input device 135. Moreover, the controller 155 may be configured to associate each orientation signal with one of the orientation blocks 160. Using the orientation signals, the controller 155 may be configured to determine the orientations of each orientation block 160, including the first orientation block 160A and the second orientation block 160B. The controller 155 may be further configured to generate the control signal to represent the orientation of the group of orientation blocks 160 in the input device 135. The controller 155 may be configured to output the control signal to the actuator 130, which as discussed above is able to control the tip of the catheter assembly 125. Upon receipt of the control signal, the actuator 130 may cause the tip of the catheter assembly 125 to adopt the orientation determined by the controller 155.

In another possible implementation shown in FIG. 4, the input device 135 may include a position block 175 configured to allow the clinician to control movement of the catheter assembly 125. For instance, the position block 175 may be configured to slide, rotate, or both, relative to one of the orientation blocks 160. The position block 175 may include a position sensor 180 configured to generate a position signal that represents the position of the position block 175. Example signals may include an advance signal that causes the catheter assembly 125 to advance, a retract signal that causes the catheter assembly 125 to retract, and a rotate signal that causes the catheter assembly 125 to rotate. The signals generated by the position block 175 may be output to the controller 155. Upon receipt of the signals, the controller 155 may be configured to generate and output an advance signal, a retract signal, and a rotate signal to the actuator 130 to control the movement of the catheter assembly 125 accordingly. Moreover, the input device 135 shown in FIG. 4 includes additional orientation blocks 160 relative to the number of orientation blocks 160 shown in FIG. 3. Each orientation block 160 is connected to at least one other orientation block 160 via a joint 165. With more orientation blocks 160, the clinician has greater control over the manipulation of the tip of the catheter assembly 125.

FIG. 5 illustrates another possible implementation of the input device 135. Instead of orientation blocks 160, the input device 135 may be formed from a flexible material that generally retains its shape until further manipulations are performed. In this implementation, orientation sensors 170 may be located throughout the input device 135 and configured to detect manipulations of various sections of the input device 135.

Figure 6:
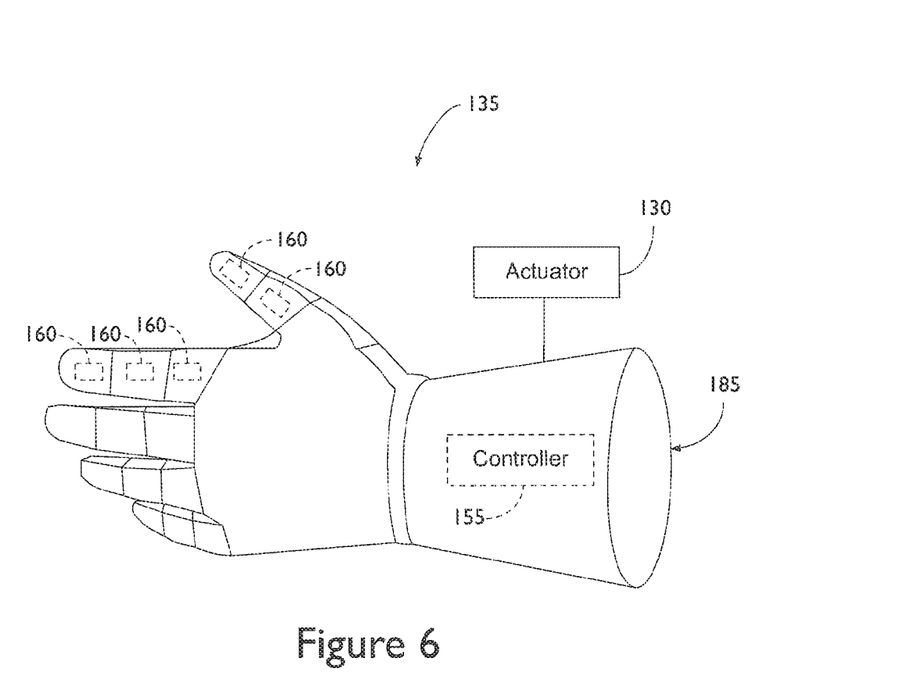
FIG. 6 illustrates an exemplary glove that may house the input device.

FIG. 6 illustrates an exemplary glove 185 that may house components of the input device 135, including the orientation blocks 160 and the controller 155. The orientation blocks 160 shown in FIGS. 3-5 may be disposed within various portions of the glove 185. In the example shown in FIG. 6, the portions of the glove 185 for receiving the clinician's thumb and index finger each include multiple orientation blocks 160. Each orientation block 160 may include an orientation sensor 170, which has been omitted from FIG. 6 for clarity. While wearing the glove 185, the clinician may move his or her fingers, and the movement may be represented by signals output by the orientation blocks 160 and provided to the controller 155. The controller 155 may be configured to determine an intended orientation of the tip of the catheter assembly 125 based at least in part on the way the clinician moves his or her hand, including his or her fingers, thumb, or both. The controller 155 may output signals to the actuator 130 that cause the catheter assembly 125 to adopt the orientation determined by the controller 155.

FIGS. 7-10 illustrate exemplary user interfaces that may be used if, e.g., the input device 135 is incorporated into a computing device. FIGS. 7-10, therefore, illustrate various exemplary user interfaces that present virtual catheter tips 190. The user interface device 150 is configured to receive a user input associated with manipulating a shape of a physical catheter tip (e.g., the tip of the catheter assembly 125 in the patient's body) based on the user's selection (see FIG. 7) or the way the user manipulates the shape of the virtual catheter tip 190 (see FIGS. 8-10). The controller 155 is configured to determine a desired shape of the physical catheter tip based on the user input and output a control signal that causes the tip of the physical catheter 140 to adopt the shape of the virtual catheter tip 190.

Figure 7:
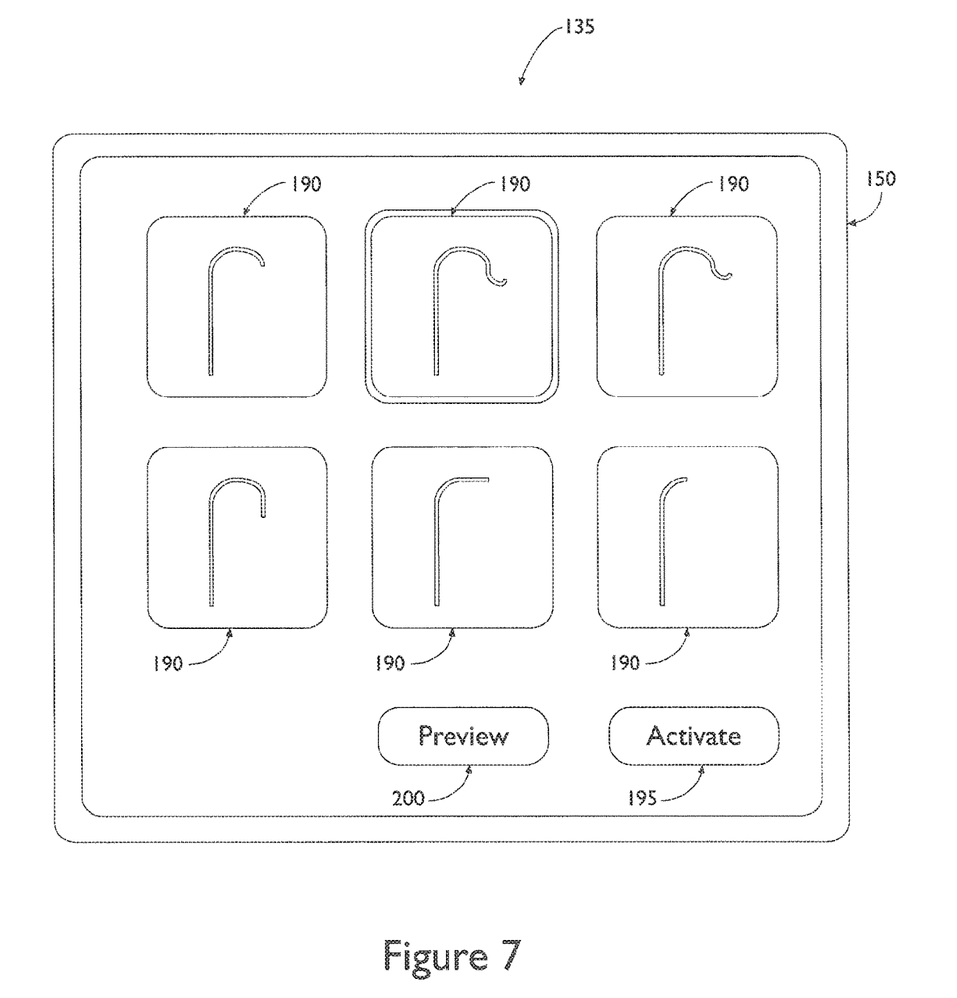
FIG. 7 illustrates an exemplary user interface for presenting shapes of virtual catheter tips.

In the exemplary approach of FIG. 7, the user interface device 150 is configured to present multiple virtual catheter tips 190 to the clinician for selection. The user interface device 150 is configured to receive a user input representing a selection of one of the virtual catheter tips 190. The user interface device 150 may present any number of predetermined shapes of virtual catheter tips 190. The user input may include a selection of one of the shapes. The user interface device 150 may be configured to highlight the shape selected by the clinician. In FIG. 7, the highlighting is represented by an extra border presented around the selected shape. The clinician may press an activate button 195 to confirm the selection and output a confirmation signal from the user interface device 150 to the controller 155. The confirmation signal may further include an indication of the selected shape. In response to receiving the confirmation signal, the controller 155 may generate and output appropriate signals to the actuator 130 that cause the physical catheter tip to adopt the selected shape.

The user interface device 150 may be further configured to present a preview of the selection to the clinician. The preview may show the clinician a path that the physical catheter tip must travel to go from its current position to a destination position based on the selected shape. The clinician may see the preview by pressing a preview button 200 after selecting one of the shapes. To generate the preview, the controller 155 may be configured to determine the current position and the destination position. The controller 155 may be cause the user interface device 150 to display an animation showing how the catheter tip will move from the current position to the destination position. In some possible approaches, the user interface device 150 may overlay the animation on an image from an image in system, such as a fluoroscopy image, of the location of the catheter 140 in the patient. This way, the clinician can see whether the movement of the catheter tip from the current position to the destination position will collide with arterial walls or other parts of the patient's body. The clinician may view the previous prior to selecting the activate button 195 so that the clinician's confirmation of the shape may include a confirmation of the path between the current position and the destination position.

Figure 8:
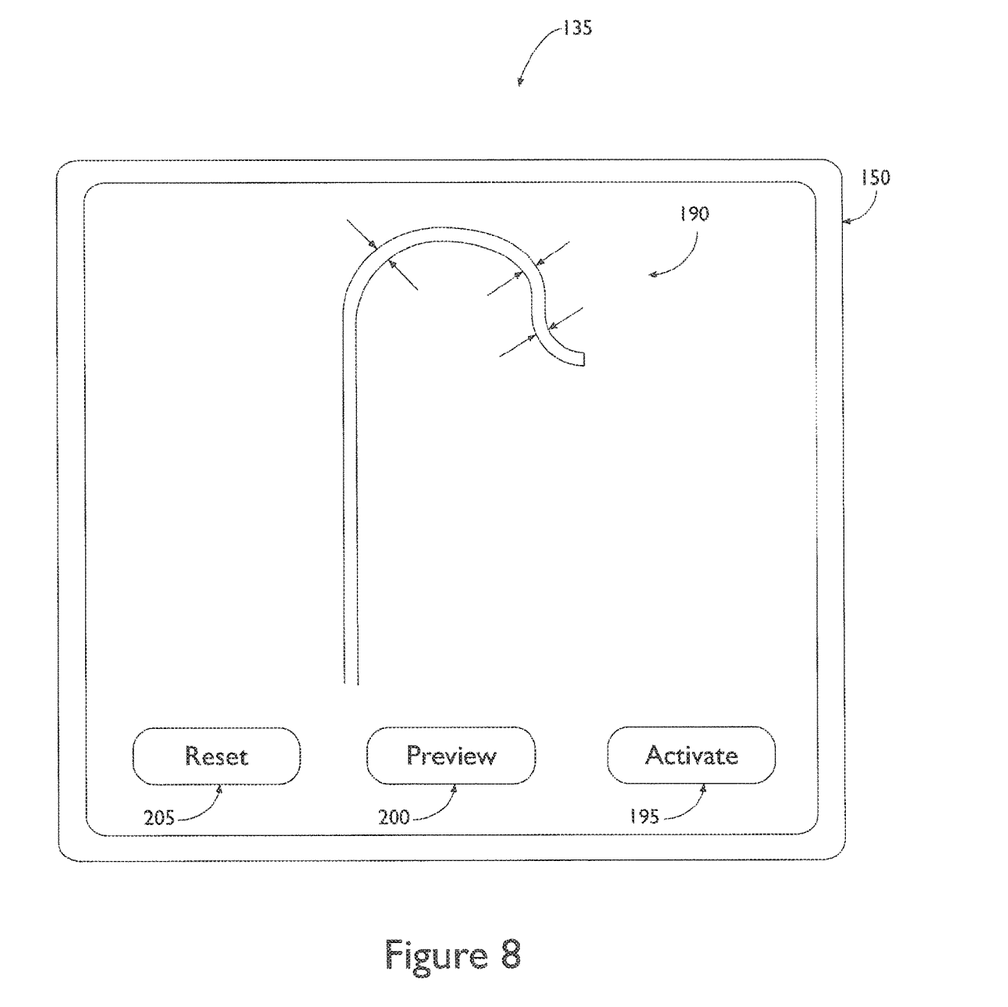
FIG. 8 illustrates an exemplary user interface for presenting a virtual catheter tip with a shape that may be manipulated via a user input.

FIG. 8 illustrates an exemplary user interface for presenting a virtual catheter tip 190 with a shape that may be manipulated via a user input including gestures. The user interface may be implemented using a touch screen. The user interface may also be implemented by using computer vision to detect hand gestures, in which case a camera may be mounted to or incorporated into the user interface device 150. The camera may provide the user interface device 150 with a field of view that allows the user interface device 150 to detect motion by, e.g., a clinician, and interpret the motion as a gesture. Other types of gestures may include the clinician virtually "pinching" or "dragging" various portions of the virtual catheter tip 190 to manipulate the shape by performing a pinch or drag gesture directly on the surface of the user interface device 150. The arrows in FIG. 8 represent some areas where the clinician may have caused the virtual catheter tip 190 to bend by performing various gestures. The clinician may view a preview of the path taken between the current shape and the destination shape by pressing the preview button 200. The reset button 205 may undo the manipulations to the virtual catheter tip 190 so that the shape of the virtual catheter tip 190 represents the shape of the physical catheter tip. The activate button 195 may cause the controller 155 to identify the desired shape of the virtual catheter tip 190 and output appropriate control signals to the actuator 130 to cause the physical catheter tip to adopt the desired shape.

Figure 9:
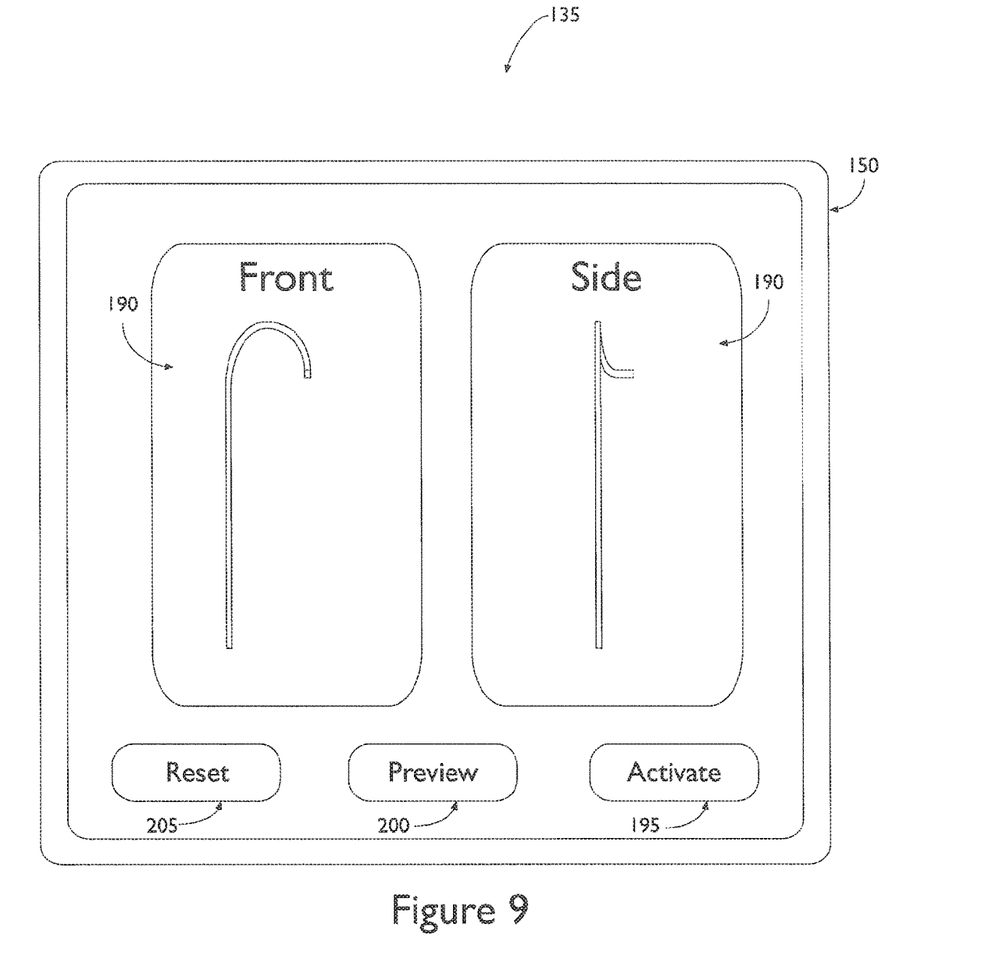
FIG. 9 illustrates an exemplary user interface for presenting different views of a virtual catheter tip.

FIG. 9 illustrates an exemplary user interface for presenting different views of the virtual catheter tip 190. FIG. 9 illustrates a front view and a side view. The user interface device 150 may be configured to present different views of the virtual catheter tip 190 so that the clinician can make changes in the shape of the virtual catheter tip 190 in multiple dimensions. The clinician may select one of the views, modify the shape of the virtual catheter tip 190 according to, e.g., gestures as discussed above, select another view, and make additional modifications until the virtual catheter tip 190 has the desired shape in multiple dimensions. Thus, each view may be modified independently of the other views. Each view may be updated when a change to one view affects the shape presented in the other views. The user may confirm the shape by pressing the activate button 195. The reset button 205 may return one or both views to the shape of the physical catheter tip. The preview button 200 may show the clinician a preview of how the physical catheter tip will move from its current position to the destination position. As discussed above, the preview may include an animation overlaid onto an internal image of the patient.

Figure 10:
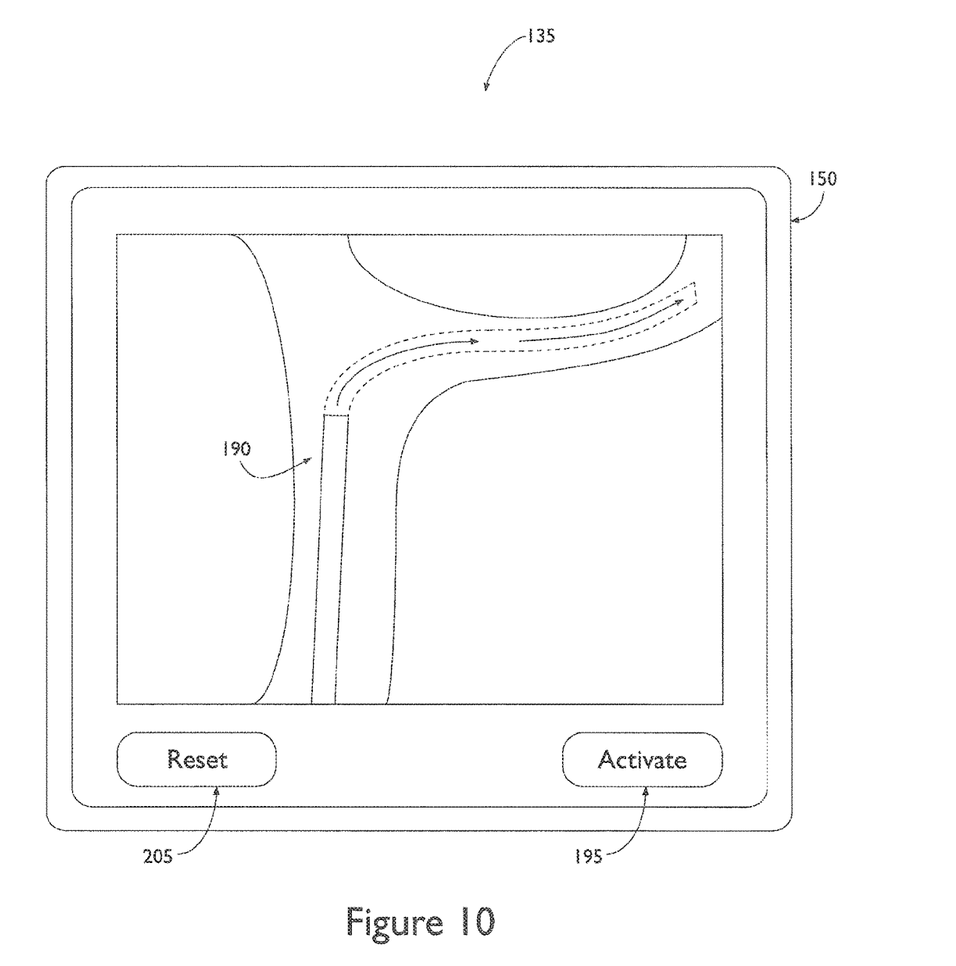
FIG. 10 illustrates an exemplary user interface for presenting a virtual catheter tip path that may be manipulated via a user input.

FIG. 10 illustrates an exemplary user interface for presenting a path of the virtual catheter tip 190 that may be manipulated via a user input including a drag gesture. The user interface device 150 may present an internal image, including a fluoroscopy image, of the physical catheter tip inside the patient's body. The user interface device 150 may be configured to receive a user input that changes the location of the physical catheter tip. The user input may include a gesture performed on the virtual catheter tip 190 shown on the user interface device 150. The arrows in FIG. 10 may represent the direction of the drag gesture performed by the clinician and the lines shown in phantom may represent the desired shape based on the drag gesture performed. The clinician may press the activate button 195 to confirm the desired shape. Once confirmed, the controller 155 may output control signals to the actuator 130 to cause the physical catheter tip to insert forward and adopt the desired shape. The clinician can press the reset button 205 to clear any modifications based on the drag gesture before the activate button 195 is pressed.

Figure 11:
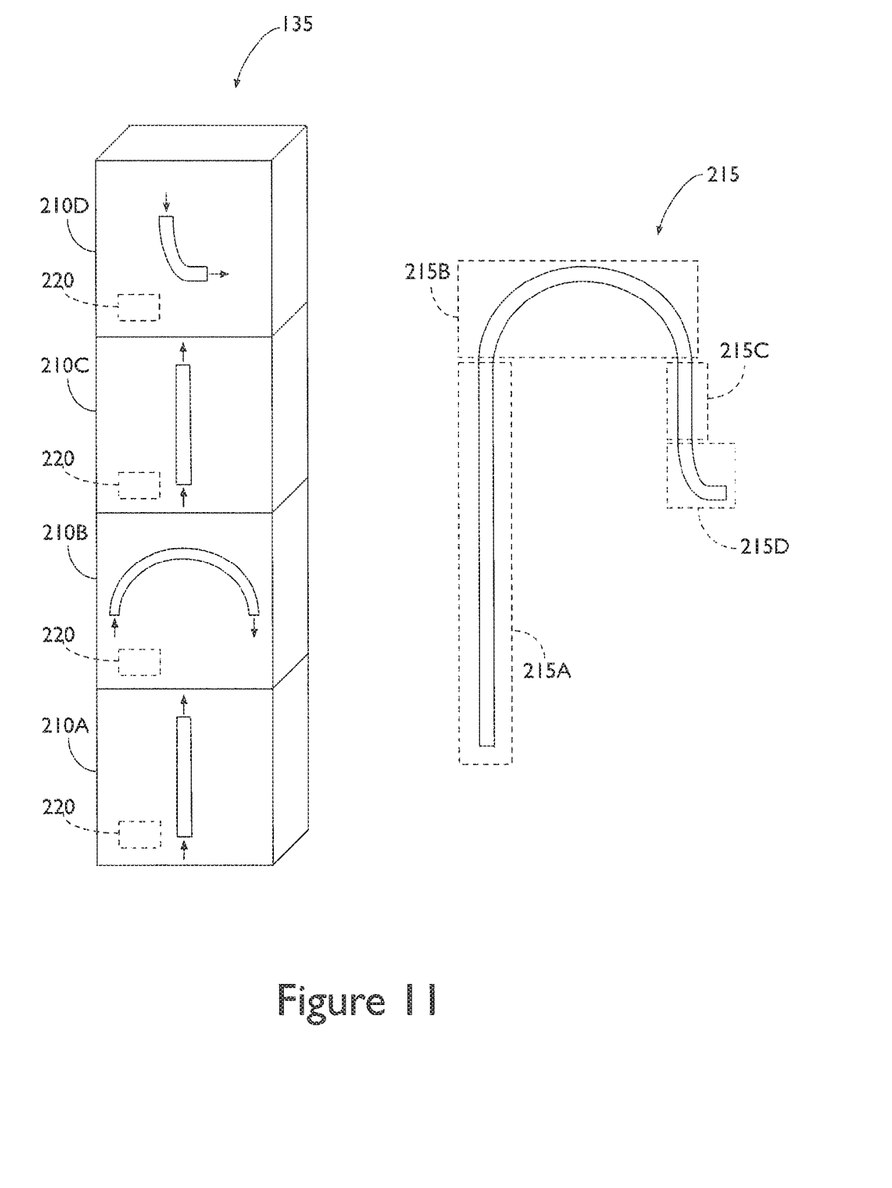
FIG. 11 illustrates an exemplary input device using stackable blocks to define a shape of a physical catheter tip.

FIG. 11 illustrates an exemplary input device 135 using stackable blocks 210 to define a shape of the physical catheter tip. Each stackable block 210 may be similar to the orientation blocks 160 discussed above and shown in FIGS. 3-5. Each stackable block 210 may represent a particular portion of the physical catheter tip 215 and may be associated with a particular shape. In the example of FIG. 11, four stackable blocks 210A, 210B, 210C, and 210D are shown, and each represents a portion of the physical catheter tip 215. That is, stackable block 210A may designate the shape of portion 215A, stackable block 210B may designate the shape of portion 215B, stackable block 210C may designate the shape of portion 215C, and stackable block 210D may designate the shape of portion 215D.

To help the clinician, each stackable block 210 may include visual instructions for developing the desired shape of the physical catheter tip 215. For instance, as shown in FIG. 11, the arrow pointing into the shape may represent how the shape connects to a shape in a previous stackable block 210, and specifically, at the location of the arrow pointing out of the shape of the previous stackable block 210. Each stackable block 210 may include a sensor 220 configured to output a presence signal indicating that the stackable block 210 is present in the stack. The presence signals may be output to the controller 155, and the control signals generated by the controller 155 may cause the actuator 130 to modify the shape of the physical catheter tip according to the presence signals received.

In general, computing systems and/or devices, such as the controller and user interface device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, and the Mac OS X operating system distributed by Apple Inc. of Cupertino, Calif. Examples of computing devices include, without limitation, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A robotics system, comprising:
   a surgical instrument having a physical distal tip;
   an actuator coupled to the surgical instrument;
   a user interface comprising a display configured to present a plurality of virtual distal tips of the surgical instrument, each of the virtual distal tips having a different distal tip shape; and
   a controller comprising a computing device communicatively coupled to the actuator and the user interface,
   wherein the user interface is configured to receive a user input designating a selected virtual tip having a selected distal tip shape from the plurality of virtual distal tips; and
   wherein the controller is configured to determine a desired shape of the physical distal tip based on the user input and output a control signal to the actuator to cause the physical distal tip to adopt the selected distal tip shape.

2. The robotic system of claim 1, wherein the surgical instrument is configured to deliver a guidewire to a surgical site of a patient.

3. The robotics system of claim 1, wherein the display comprises a touchscreen display configured to present a graphical user interface as well as receive the user input.

4. The robotics system of claim 1, wherein the user interface is further configured to receive a user input confirming the selected virtual distal tip.

5. The robotics system of claim 4, wherein the controller is further configured to receive a confirmation signal prior to generating the control signal to the actuator.

6. The robotics system of claim 1, wherein the actuator comprises of an instrument driver configured to at least one of advance, retract, manipulate, and rotate the surgical instrument.

7. The robotics system of claim 6, wherein the instrument driver comprises of a motor configured to tension a pull wire in the surgical instrument that causes a portion of the surgical instrument to articulate in a selected direction.

8. The robotics system of claim 1, wherein the user interface is further configured to present a preview of the virtual distal tip within a surgical site of a patient.

9. The robotics system of claim 8, wherein the preview comprises an animation showing how the physical tip will move from a current position to a destination position.

10. The robotics system of claim 9, wherein the animation is overlaid on an image of the surgical site.

11. A method comprising:
presenting a plurality of virtual distal tips on a display of a user interface, each of the virtual distal tips having a unique distal tip shape;
receiving from a user via the user interface a user input designating a selected virtual tip having a selected distal tip shape from the plurality of virtual distal tips;
determining a desired shape of the physical distal tip based on the user input; and
outputting from a controller a control signal to cause an actuator to actuate a surgical instrument so that the physical distal tip adopts the selected distal tip shape.

12. The robotic system of claim 11, wherein the surgical instrument is configured to deliver a guidewire to a surgical site of a patient.

13. The method of claim 11, wherein the display is a touchscreen display configured to present a graphical user interface as well as receive the user input.

14. The method of claim 11, further comprising receiving from the user via the user interface a user input confirming the selected virtual distal tip.

15. The method of claim 14, further comprising receiving by the controller a confirmation signal prior to outputting the control signal from the controller.

16. The method of claim 11, wherein the actuator comprises of an instrument driver configured to at least one of advance, retract, manipulate, and rotate the surgical instrument.

17. The method of claim 16, wherein the instrument driver comprises of a motor configured to tension a pull wire in the surgical instrument that causes a portion of the surgical instrument to articulate in a selected direction.

18. The method of claim 11, further comprising presenting a preview via the user interface of the virtual distal tip within a surgical site of a patient.

19. The method of claim 18, wherein the preview comprises of an animation showing how the physical tip will move from a current position to a destination position.

20. The method of claim 19, wherein the animation is overlaid on an image of the surgical site.

* * * * *

UNITED STATES PATENT AND TRADEMARK OFFICE
CERTIFICATE OF CORRECTION

PATENT NO. : 10,123,843 B2
APPLICATION NO. : 15/393898
DATED : November 13, 2018
INVENTOR(S) : Serena H. Wong Page 1 of 1

It is certified that error appears in the above-identified patent and that said Letters Patent is hereby corrected as shown below:

In the Claims

In Column 10, Line 52, Claim 2, change "robotic" to --robotics--.

In Column 11, Line 25, Claim 12, change "robotic system" to --method--.

Signed and Sealed this
Fifth Day of March, 2019

Andrei Iancu
*Director of the United States Patent and Trademark Office*